(12) United States Patent
Spodsberg

(10) Patent No.: US 9,109,215 B2
(45) Date of Patent: Aug. 18, 2015

(54) POLYPEPTIDES HAVING XYLANASE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/765,222

(22) Filed: Feb. 12, 2013

(65) Prior Publication Data

US 2014/0227760 A1   Aug. 14, 2014

(51) Int. Cl.
  *C12N 9/24* (2006.01)
  *C12P 7/06* (2006.01)
  *C12P 7/14* (2006.01)

(52) U.S. Cl.
  CPC ....... *C12N 9/2482* (2013.01); *C12Y 302/01008* (2013.01)

(58) Field of Classification Search
  CPC .................................................... C12N 9/248
  USPC ................................ 435/99, 162, 200, 252.3
  See application file for complete search history.

(56) References Cited

U.S. PATENT DOCUMENTS

2014/0230097 A1 *   8/2014   Spodsberg .................... 800/298

FOREIGN PATENT DOCUMENTS

DK   WO9727290 A1 *   7/1997   ............... C12N 9/24

OTHER PUBLICATIONS

Fernndes et al., Homologous xylanases from *Clostridium thermocellum*: evidence for bi-functional activity, synergism between xylanase catalytic modules and the presence of xylan-binding domains in enzyme complexes. Biochem. J. 342: 105-110, 1999.*

Fanutti et al., The Conserved Noncatalytic 40-Residue Sequence in Cellulases and Hemicellulases from Anaerobic Fungi Functions as a Protein Docking Domain. The Jnl. of Biol. Chem. 270: 49, 29314-29322, 1995.*

* cited by examiner

*Primary Examiner* — Tekchand Saidha
(74) *Attorney, Agent, or Firm* — Robert L. Starnes

(57) ABSTRACT

The present invention relates to isolated polypeptides having xylanase activity and polynucleotides encoding the polypeptides. The invention also relates to nucleic acid constructs, vectors, and host cells comprising the polynucleotides as well as methods of producing and using the polypeptides.

20 Claims, No Drawings

POLYPEPTIDES HAVING XYLANASE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having xylanase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Xylanases degrade beta-1,4-xylan into xylose, thus breaking down hemicellulose, one of the major components of plant cell walls.

There is a need in the art to improve cellulolytic and hemicellulolytic enzyme compositions through supplementation with additional enzymes to increase efficiency and to provide cost-effective enzyme solutions for degradation of lignocellulose.

The present invention provides polypeptides having xylanase activity and polynucleotides encoding the polypeptides.

SUMMARY OF THE INVENTION

The present invention relates to isolated polypeptides having xylanase activity selected from the group consisting of:

(a) a polypeptide having at least 77% sequence identity to the mature polypeptide of SEQ ID NO: 2, or a polypeptide having at least 81% sequence identity to the mature polypeptide of SEQ ID NO: 4, or a polypeptide having at least 74% sequence identity to the mature polypeptide of SEQ ID NO: 6;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, or SEQ ID NO: 5, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, or SEQ ID NO: 5; or the cDNA sequence thereof;

(d) a variant of the mature polypeptide of SEQ ID NO: 2, SEQ ID NO: 4, or SEQ ID NO: 6 comprising a substitution, deletion, and/or insertion at one or more (e.g., several) positions; and (e) a fragment of the polypeptide of (a), (b), (c), or (d) that has xylanase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 18 to 349 of SEQ ID NO: 2), a catalytic domain having at least 60% sequence identity to the catalytic domain of SEQ ID NO: 4 (for example, amino acids 81 to 376 of SEQ ID NO: 4), or a catalytic domain having at least 60% sequence identity to the catalytic domain of SEQ ID NO: 6 (for example, amino acids 82 to 396 of SEQ ID NO: 6);

(b) a catalytic domain encoded by a polynucleotide having at least 60% sequence identity to the catalytic domain coding sequence of SEQ ID NO: 1 (for example, nucleotides 52-246, 300-390, 444-570, 624-625, 685-705, 764-1272, and 1333-1383 of SEQ ID NO: 1), a catalytic domain encoded by a polynucleotide having at least 60% sequence identity to the catalytic domain coding sequence of SEQ ID NO: 3 (for example, nucleotides 353-440, 493-548, 603-609, 667-756, 808-833, 885-980, 1037-1182, 1247-1355, 1408-1480, 1538-1557, 1613-1699, and 1754-1843 of SEQ ID NO: 3), or a catalytic domain encoded by a polynucleotide having at least 60% sequence identity to the catalytic domain coding sequence of SEQ ID NO: 5 (for example, nucleotides 426-569, 635-725, 796-922, 977-978, 1041-1061, 1109-1617, and 1677-1727 of SEQ ID NO: 5);

(c) a variant of a catalytic domain comprising a substitution, deletion, and/or insertion of one or more (several) amino acids of the catalytic domain of SEQ ID NO: 2, SEQ ID NO: 4, or SEQ ID NO: 6; and (d) a fragment of a catalytic domain of (a), (b), or (c), which has xylanase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The present invention also relates to a polynucleotide encoding a signal peptide comprising or consisting of amino acids 1 to 17 of SEQ ID NO: 2, amino acids 1 to 20 of SEQ ID NO: 4, or amino acids 1 to 19 of SEQ ID NO: 6, which is operably linked to a gene encoding a protein; nucleic acid constructs, expression vectors, and recombinant host cells comprising the polynucleotides; and methods of producing a protein.

```
                            Sequences of the invention

Lentinus similis Strain NN048945 Genomic Nucleotide Sequence (SEQ ID NO: 1):
         1  ATGAGAACTA ATCTCGTGGC CCTGCTGTCG GCGATATCAC TCGCAGCATC CGCCCCAACA TTCAACGGGA CCCTAGAAGG
        81  ACGAGCGGCA CAAGCCACAG AGCTTCATGC CCTTGCCAAA CAACATGGCA AACTGTACTT CGGCACAGCA ACGGACAACC
       161  CAGAGCTCAC CGACACGCCG TATGTTGCCA TCCTCGACGA CAACCAAATG TTCGGTCAAA TCACAGCTGC CAACAGTATG
       241  AAATGGGTAA GCATTTGCCT GCGAGGAGAA TGGCCGTTGC TGATGTTCTT TCATATTAGG ACGCGACTGA ACCTTCCCGT
       321  GGCCAGTTTA CGTTTGCCGC AGGCGACGTC ATTGCGAACC TGGCCAAGCA GAATGGGCAA TTGCTTCGAG GTGTGTCAAG
       401  CCTGTTTCTA GATTTCACGG TTCGCCTAAC AATACATGAT TAGGGCATAA TTGCTTCGAG CACAACCAGT TGCCAAGCTG
       481  GGTGACCGCA GGTCACTTCT CCAAGGCGGA CTTGCTATCG ATTGTTCAGA CCCACTGCAG CACCCTGGTT GGACATTACA
       561  AGGGACAAGT GTAAGTCTGC TACTACACCG ATCGAAAGCT AACGGACTCA CGTTCTCTCC TAGCTGTGAG TCTAAGGGCA
       641  TACTACCTTG ACACATACTC AAGTACTGAC GTTAATAACT GAAGACGCTT GGGATGTCGT CAATGGTATG TTCACAGTGC
       721  ATCTCGGTGT GGACTGCATC CCAACCGCAT TCCACATAAT CAGAGATCAT GAATGACAAC GGCACATTTG CGAACGACGT
       801  CTTCTTCAGC ACTACAGGGA CAGATTACAT CTCGCGCTG CTCGCGCCGC TGACCCTAAT GCCAAACTAT
       881  ATGCAAACGA CTTCAATATC GAAGGCACTG GCGCAAAATC AACCGCGTAC CAAAATCTCA TCCGTACTCT CAAATCCCAA
       961  GGTGTACCCA TCGACGGCAT CGGCATGCAA TCTCACTTCA TCGTCGGGGA GCTCCCGCCA AACATCAAAC AGAACATACA
      1041  GGCTTTCACC GCGCTGGGTG TGGAAGTGGC GATTACAGAG TTGGATGTGA GGATGACTTT GCCTGCTACT CAGGCATTGT
      1121  TGCAACAGCA GCAGAAGGAT TATCAGACGG TGATCCAGGC TTGCAACGAG GTCCCGGGAT GCATCGGTGT TACACTTTGG
      1201  GATTTCACGG ATAAGTTCTC GTGGGTGCCT GGCGCGTTCC CCGGACAGGG GGCTGCATGC CCTTGGGATC AGGTACGTAC
      1281  CGGAAGTTCT CACTGTGAAA TGATCTCTAA CGTGCTCACG TACCAATCAC AGAATTTGCA ACTCAAGCCT GCCTTCACCG
      1361  GTATTGTCAA TGGCTTCAAC TCATGA Exons/Introns (in base pairs) of SEQ ID NO: 1:
Exon 1             1-246 bp
Intron 1           247-299 bp
Exon 2             300-390 bp
Intron 2           391-443 bp
Exon 3             444-570 bp
Intron 3           571-623 bp
Exon 4             624-625 bp
Intron 4           626-684 bp
Exon 5             685-705 bp
Intron 5           706-763 bp
Exon 6             764-1272 bp
Intron 6           1273-1332 bp
Exon 7             1333-1386 bp Features (in base pairs) of SEQ ID NO: 1:
Signal Peptide           1-51 bp
Xylanase                 52-246, 300-390, 444-570, 624-625, 685-705, 764-1272, 1333-1383 bp
catalytic site
Stop codon               1384-1386 bp Protein Sequence of Lentinus similis Strain NN048945 protein (SE) ID NO: 2):
         1  MRTNLVALLS AISLAASAPT FNGTLEGRAA QATELHALAK QHGKLYFGTA TDNPELTDTP
        61  YVAILDDNQM FGQITAANSM KWDATEPSRG QFTFAAGDVI ANLAKQNGQL LRGHNCVWHN
       121  QLPSWVTAGH FSKADLLSIV QTHCSTLVGH YKGQVYAWDV VNEIMNDNGT FANDVFFSTT
       181  GTDYIATAFR AARAADPNAK LYANDFNIEG TGAKSTAYQN LIRTLKSQGV PIDGIGMQSH
       241  FIVGELPPNI KQNIQAFTAL GVEVAITELD VRMTLPATQA LLQQQQKDYQ TVIQACNEVP
       301  GCIGVTLWDF TDKFSWVPGA FPGQGAACPW DQNLQLKPAF TGIVNGFNS Features of SEQ ID NO: 2 (amino acid positions):
Signal Peptide              1-17
Xylanase catalytic site     18-349

Signal Peptide Sequence of SEQ ID NO: 2:
MRTNLVALLSAISLAAS

Lentinus similis Strain NN048945 Genomic Nucleotide Sequence (SEQ ID NO: 3):
         1  ATGAAGTCCC TCGCTGCCTT CGTCGCTTTA GCCGCTGCTT TGTCTGGCTC TGCCAACGCA GTAGCAGTTT GGGGCCAATG
        81  TATGTCGCGT CCTATCATCC TGTTCCTCAC TTTTCGCTAA CTACATTATT GTCTCAGGCG GGTATGTCA AATTCCTGCT
       161  ATGTTAACGA ATGGCGGTAT TGAGAGAGAT TAGGGCATTG GTTATTCCGG GTCGACTGTC TGCGACGCAG GCACTACATG
       241  TGTCAAGTTG AATGACTACT ACTCCCAATG CCAGCCTGGG GCTGCCACAT CGCCACCCGC GACGACATCA CAACCGGCCC
       321  CCACAGGTTC GCCCGCTCCC GCCGCGAGTG GACTGGCCGC CGCTTTTGCT AAAAAGGGCA AGTTGTICTG GGGAACTGCA
       401  TCGGACTCCA ACAGATTCAA CGACGCAAAG GATTCCCAAG GTAAACACGC ACTTCACAAC GGATAATGCC CTTACTCAGG
       481  ACGCCCATTC AGTGACAATC GCCAACTTCA ACAGTCTTAC CCCCGAAAAC TCCATGAAGT GGGATGCAGT AAGCGTTGTT
       561  CTTCTCATCA TCGGACGTGA TCCATATTGA TTGTATATGC AGACTGAGCG TAAGTTTGCG GTTGTAAATG TTCCCTATTG
       641  GTTGTAAATG CCACTATTCT CCATAGCCAG CCGTGGTCAG TTCTCCTTCT CTGGTGCGGA CGCACTAGTC AACTACGCCA
       721  GCCAGCACGG AATGTTAGTT CGTGCTCACA CGTTGGGTTT GTCGTTCATA CCTCAGGTCG AATGTGCGTA GACTGACATA
       801  TCTCCAGTTT GGCATTCTCA GCTCCCATCA TGGGTATGAT CATTGGACAT GTCGTCCTTT ATCAGCTACT CATTCGGAGT
```

| Sequences of the invention |
|---|
| 881 CTAGGTCTCT TCCATTTCGG ACAAAACAAC GCTGACCTCA GTCATTCAAA ACCACATTTC CACTGTCGCC GGAAGATATA
 961 AAGGAAAGGT TAAGTTTGCG GTATGTACTA CCTCTTTCAC CTCGAAGCGT GTCATATATC TGATTATTCC TGACAGGATG
1041 TTGTCAACGA GATCTTCAAC GAGGATGGAA CGTTCCGCTC ATCCGTCTTC TACAATGTGC TCGGCCAAAG CTTCGTTACT
1121 CTCGCGTTCC AAGCTGCCAG GCAAGCAGAT CCTAACGCCA AGCTGTACAT CAACGACTAC AAGTAGGTCA CTACGCGGCC
1201 TATTGTTGAA CGGTTCATGC AATTAATTGA CAACAATCGT GTACAGCTTG GATAGCGCCA ATGCCAAGTT GACGGCCGTT
1281 GTACAGCTTG TGAAGCAGAT TAACAATAGC GGTACGAAGC TCATCGACGG TATCGGTACT CAGATGCACC TCTCGGTTCG
1361 TTACCAAACC AATTGTTTGT TACGATAGTT GTGCTTATTT CATCCAGGCT GGAGGCGCGG GAGGTGCCCA GGCGGCTCTC
1441 CAGCTTGCTG CGACTGCTGG TGTCGAGGIT GCTATCACCG GTGAGTTATT GCAGGGCATG AACGTGATCG CAGGATACTG
1521 ATATCACTTC GATCCAGAAT TGGATATTGC GAATGCTGTA CGTCTTTTCA CGCTACTTGA GGCATAACTT TTTTGACGTG
1601 GCCTTTCCTC AGGCCCCCAA CGACTATGTT ACCGTCGTGA AAGCTTGCTT GGCTGTCTCT AACTGCGTAT CTATCACGAG
1681 CTGGGGTGTC AGTGACAAGG TCAGGCATCC TTTGCTCACC TTTGCTACCT ATACAGCTGA ACTTTCCTCG CAGGACTCTT
1761 GGCGTGCATC CACGAACCCT CTGCTCTTCG ATGCTAACTT TAACCCTAAG CCTGCATACA CTGCCATCTT GCAGGCACTT
1841 GCCTAA |

Exons/Introns (in base pairs) of SEQ ID NO: 3:
Exon 1        1-79 bp
Intron 1      80-137 bp
Exon 2        138-176 bp
Intron 2      177-230 bp
Exon 3        231-440 bp
Intron 3      441-492 bp
Exon 4        493-548 bp
Intron 4      549-602 bp
Exon 5        603-609 bp
Intron 5      610-666 bp
Exon 6        667-756 bp
Intron 6      757-807 bp
Exon 7        808-833 bp
Intron 7      834-884 bp
Exon 8        885-980 bp
Intron 8      981-1036 bp
Exon 9        1037-1182 bp
Intron 9      1183-1246 bp
Exon 10       1247-1355 bp
Intron 10     1356-1407 bp
Exon 11       1408-1480 bp
Intron 11     1481-1537 bp
Exon 12       1538-1557 bp
Intron 12     1558-1612 bp
Exon 13       1613-1699 bp
Intron 13     1700-1753 bp
Exon 14       1754-1846 bp Features (in base pairs) of SEQ ID NO: 3:
Signal Peptide              1-60 bp
Cellulose Binding           61-79, 138-176, 231-277 bp
Module 1 (CBM 1)
Linker                      278-352 bp
Xylanase                    353-440, 493-548, 603-609, 667-756, 808-833, 885-980, 1037-1182,
catalytic site              1247-1355, 1408-1480, 1538-1557, 1613-1699, 1754-1843 bp
Stop codon                  1844-1846 bp Protein Sequence of *Lentinus similis* Strain NN048945 protein (SEQ ID NO: 4):
  1 MKSLAAFVAL AAALSGSANA VAVWGQCGVC QIPAMLTNGG TTCVKLNDYY SQCQPGAATS
 61 PPATTSQPAP TGSPAPAASG LAAAFAKKGK LFWGTASDSN RFNDAKDSQV TIANFNSLTP
121 ENSMKWDATE PSRGQFSFSG ADALVNYASQ HGMLVRAHTL VWHSQLPSWV SSISDKTTLT
181 SVIQNHISTV AGRYKGKVRS WDVVNEIFNE DGTFRSSVFY NVLGQSFVTL AFQAARQADP
241 NAKLYINDYN LDSANAKLTA VVNLVKQINN SGTKLIDGIG TQMHLSAGGA GGAQAALQLA
301 ATAGVEVAIT ELDIANAAPN DYVTVVKACL AVSNCVSITS WGVSDKDSWR ASTNPLLFDA
361 NFNPKPAYTA ILQALA Features of SEQ ID NO: 4 (amino acid positions):
Signal Peptide              1-20
Cellulose Binding           21-55
Module 1 (CBM 1)
Linker                      56-80
Xylanase catalytic site     81-376

Signal Peptide Sequence of SEQ ID NO: 4:
MKSLAAFVALAAALSGSANA

*Lentinus similis* Strain NN048945 Genomic Nucleotide Sequence (SEQ ID NO: 5):
  1 ATGAAGCTTT CTGGTACGCT TGCCGCTCTT ATCGCCATTC TCCCCTTTGC AGCTGCACAA TCTCAAGAGT GGGGTCAATG
 81 TAAGCCTTCC ATACGACTCA TCGTTAGTGA AACTGTGGAT TGCTGACTCT TATTTCAATA GGTGGCGGGA TTGTGAGTAT
161 ATATAGGTCT TTTCAGGCAA CTTTGCAATA TGAAGCTCAG AATCCTGTAG GGCTGGACTG GTCCGACAAC ATGCGTTGCC -continued Sequences of the invention

```
 241 GGAACCATCT GTGICAAGCA GAACGATTAC TACTCTCAGT GCCTTCCATC TGTCAGTCTG CCATCATGCG TCCTCATGAA
 321 GACGTCTTTG ACTCAGTTAC ATGTTTTATT TAGACCTCGG TTCCCACTTC CGTTCCCCCG CCTACCAGCA CCGTGTCTTC
 401 ACCTGGATCG ACGCCAACGG CAGGTCTCAA TAGTATCGCC CAGGCCCATG GCCTGACCTA CTTCGGCTCT GCCACGGACA
 481 ACCCAGAGCT TTCTGACCAG GCCTATGTCG CCATCCTCAG CGACAACACT ATGITCGGTC AGATCACACC TGGAAACAGT
 561 ATGAAATGGG TACGTTCGTG GCTCAAGCAT GCAGGGAGTA CGCGACTGAC CAGCAACATT ATTTGGAATC GTAGGATGCT
 641 ACTGAGCCTT CTCGAGGTAC TTTCACTTTC TCCGGAGGTG ATGTGATCGC AAACCTCGCC AAGACGAATG GGCAATTGCT
 721 CCGAGGTATG CACGCTITCA TTCATTCTCT ACATGGGATG GAAAGATAC GGTACTTATG ACGGTTCTCT CGTAGGGCAT
 801 AACTGTGTTT GGTACAATCA GCTTCCTTCC TGGGTATCCT CTGGAAACTT CGATGCTCCC ACCTTGACGT CCATCGTGCA
 881 GACTCATTGC ACCACTCCCG TTGGTGGAATT CAAGGGTCAA ATGTGAGTAA TTCTATTTCT ATGATCTCCG AAACAGACTG
 961 AATGATGCTC TTTCAGTTGT GTGTGGAATT CAATGCGCG ATCATAACGT TGACTGATGT TTTGCTTTGA CATTCGAAAG
1041 ATTCTTGGGA TGTTATCAAC GGTGAGTTAT TCTCTCGCCG TCCCTGAGCT TGTATCTAAC TCGAACAGAA CCCTTCAACG
1121 ATGACGGTAC TTGGCGCCAG GACGTCTTCT ACAACGTATT GGGCACAAGC TACGTTCAGA TTGCCTTAGA GGCTGCCCGT
1201 GCTGCCGACC CTGCGGCCAA GCTGTACATT AACGACTACA ACATCGAAGG TCCTGGAGCC AAGGCCACCG CCATGCAGAA
1281 CCTCATCAAG ACCCTCAAGA CCAACAACGT ACCCATCGAT GGTGTCGGTC TTCAAGGTCA CTTCATCGTC GGCGCTCTCC
1361 CCTCTGGCAT TCAGCAGAAC ATCCAGGCTT TCGTGAACCT CGGCGTTGAG GTCGCCATCA CCGAGCTAGA TATTAGGACG
1441 ACCACTCCCG CGTCGTCTTC TGCTCTTCAG CAGCAGGCGA AGGATTATGC GACTGTGGTC ACGGCATGTC GTGCTGTGAA
1521 GGGTTGTATT GGTATCACCG TCTGGGACTA CACAGACAAG TACTCTTGGG TTCCGTCGAC CTTCTCTGGT CAGGGTGCTG
1601 CTTGCCCGTG GGACCAGGTG AGTTATCTAT AGGCTTCTCT GCTGTGTACT GCGGTCTGAG ACGCGCCGAC CCGCAGAACC
1681 TCCAACCAAA GCCAGCGTAC ACCAGTATTG CACAATCGTT GGCTGCCTAA
```

Exons/Introns (in base pairs) of SEQ ID NO: 5:
Exon 1      1-79 bp
Intron 1    80-141 bp
Exon 2      142-152 bp
Intron 2    153-210 bp
Exon 3      211-291 bp
Intron 3    292-353 bp
Exon 4      354-569 bp
Intron 4    570-634 bp
Exon 5      635-725 bp
Intron 5    726-795 bp
Exon 6      796-922 bp
Intron 6    923-976 bp
Exon 7      977-978 bp
Intron 7    979-1040 bp
Exon 8      1041-1061 bp
Intron 8    1062-1108 bp
Exon 9      1109-1617 bp
Intron 9    1618-1676 bp
Exon 10     1677-1730 bp Features (in base pairs) of SEQ ID NO: 5:
Signal Peptide              1-57 bp
Cellulose Binding           58-79, 142-152, 211-288 bp
Module 1 (CBM 1)
Linker                      289-291, 354-425 bp
Xylanase                    426-569, 635-725, 796-922, 977-978, 1041-1061, 1109-1617,
catalytic site              1677-1727 bp
Stop codon                  1728-1730 bp Protein Sequence of *Lentinus similis* Strain NN048945 protein (SEQ ID NO: 6):
```
  1 MKLSGTLAAL IAILPFAAAQ SQEWGQCGGI GWTGPTTCVA GTICVKQNDY YSQCLPSTSV
 61 PTSVPPPTST VSSPGSTPTA GLNSIAQAHG LTYFGSATDN PELSDQAYVA ILSDNTMFGQ
121 ITPGNSMKWD ATEPSRGTFT FSGGDVIANL AKTNGQLLRG HNCVWYNQLP SWVSSGNFDA
181 PTLTSIVQTH CSTLVGHYKG QIYSWDVINE PFNDDGTWRQ DVFYNVLGTS YVQIALEAAR
241 AADPAAKLYI NDYNIEGPGA KATAMQNLIK TLKTNNVPID GVGLQGHFIV GALPSGIQQN
301 IQAFVNLGVE VAITELDIRT TTPASSSALQ QQAKDYATVV TACRAVKGCI GITVWDYTDK
361 YSWVPSTFSG QGAACPWDQN LQPKPAYTSI AQSLAA
```

Features of SEQ ID NO: 6 (amino acid positions):
Signal Peptide              1-19
Cellulose Binding           20-56
Module 1 (CBM 1)
Linker                      57-81
Xylanase catalytic site     82-396

Signal Peptide Sequence of SEQ ID NO: 6:
MKLSGTLAALIAILPFAAA

DEFINITIONS

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer. In one aspect, the polypeptides of the present invention have at least 20%, e.g., at least 40%, at least 50%, at least 60%, at least 70%, at least 80%, at least 90%, at least 95%, or at least 100% of the xylanase activity of the mature polypeptide of SEQ ID NO: 2, SEQ ID NO: 4, or SEQ ID NO: 6.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, J. Bacteriol. 180: 243-249. One unit of alpha-glucuronidase equals the amount of enzyme capable of releasing 1 µmole of glucuronic or 4-O-methyl-glucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has xylanase activity. In one aspect, a fragment contains at least 20 amino acid residues, e.g., at least 30 to 348 amino acid residues or at least 50 to 340, 80 to 310, 100 to 290, 150 to 270, or 200 to 250, or any number in between, amino acid residues of SEQ ID NO: 2. In another aspect, a fragment contains at least 20 amino acid residues, e.g., at least 30 to 375 amino acid residues or at least 50 to 370, 80 to 350, 100 to 320, 150 to 300, or 200 to 250, or any number in between, amino acid residues of SEQ ID NO: 4. In another aspect, a fragment contains at least 20 amino acid residues, e.g., at least 30 to 395 amino acid residues or at least 50 to 390, 80 to 360, 100 to 340, 150 to 300, or 200 to 250, or any number in between, amino acid residues of SEQ ID NO: 6.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 349 of SEQ ID NO: 2 based on the SignalP program (Nielsen et al., 1997, *Protein Engineering* 10:1-6) that predicts amino acids 1 to 17 of SEQ ID NO: 2 are a signal peptide. In another aspect, the mature polypeptide is amino acids 1 to 349 of SEQ ID NO: 2. In another aspect, the mature polypeptide is amino acids 21 to 376 of SEQ ID NO: 4 based on the SignalP program that predicts amino acids 1 to 20 of SEQ ID NO: 4 are a signal peptide. In another aspect, the mature polypeptide is amino acids 1 to 376 of SEQ ID NO: 4. In another aspect, the mature polypeptide is amino acids 20 to 396 of SEQ ID NO: 6 based on the SignalP program that predicts amino acids 1 to 19 of SEQ ID NO: 6 are a signal peptide. In another aspect, the mature polypeptide is amino acids 1 to 396 of SEQ ID NO: 6. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 52 to 1383 of SEQ ID NO: 1 or the cDNA sequence thereof based on the SignalP program (Nielsen et al., 1997, supra) that predicts nucleotides 1 to 51 of SEQ ID NO: 1 encode a signal peptide. In another aspect, the mature polypeptide coding sequence is nucleotides 1 to 1383 of SEQ ID NO: 1 or the cDNA sequence thereof. In another aspect, the mature polypeptide coding sequence is nucleotides 61 to 1843 of SEQ ID NO: 3 or the cDNA sequence thereof based on the SignalP program that predicts nucleotides 1 to 60 of SEQ ID NO: 3 encode a signal peptide. In another aspect, the mature polypeptide coding sequence is nucleotides 1 to 1843 of SEQ ID NO: 3 or the cDNA sequence thereof. In another aspect, the mature polypeptide coding sequence is nucleotides 58 to 1727 of SEQ ID NO: 5 or the cDNA sequence thereof based on the SignalP program that predicts nucleotides 1 to 57 of SEQ ID NO: 5 encode a signal peptide. In another aspect, the mature polypeptide coding sequence is nucleotides 1 to 1727 of SEQ ID NO: 5 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 21 to 55 of SEQ ID NO: 4. In one embodiment the CBM is amino acids 20 to 56 of SEQ ID NO: 6. The CBM is separated from the catalytic domain by a linker sequence. The linker is in one embodiment amino acids 56 to 80 of SEQ ID NO: 4. The linker is in one embodiment amino acids 57 to 81 of SEQ ID NO: 6.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having xylanase activity. In one aspect, a subsequence contains at least 800 nucleotides, e.g., at least 1000 nucleotides or at least 1100 nucleotides of SEQ ID NO: 1. In another aspect, a subsequence contains at least 1000 nucleotides, e.g., at least 1200 nucleotides or at least 1500 nucleotides of SEQ ID NO: 3. In another aspect, a subsequence contains at least 1000 nucleotides, e.g., at least 1200 nucleotides or at least 1500 nucleotides of SEQ ID NO: 5.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

DETAILED DESCRIPTION OF THE INVENTION

Polypeptides Having Xylanase Activity

In an embodiment, the present invention relates to isolated polypeptides having a sequence identity to the mature polypeptide of SEQ ID NO: 2 of at least 77%, e.g., at least 78%, at least 79%, at least 80%, at least 85%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 4 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have xylanase activity. In an embodiment, the present invention relates to isolated polypeptides having a sequence identity to the mature polypeptide of SEQ ID NO: 6 of at least 74%, e.g., at least 75%, at least 76%, at least 77%, at least 80%, at least 85%, at least 87%, at least 88%, at least 89%, at least 90%, at least 91%, at least 92%, at least 93%, at least 94%, at least 95%, at least 96%, at least 97%, at least 98%, at least 99%, or 100%, which have xylanase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, or SEQ ID NO: 6.

A polypeptide of the present invention preferably comprises or consists of the amino acid sequence of SEQ ID NO: 2, SEQ ID NO: 4, or SEQ ID NO: 6 or an allelic variant thereof; or is a fragment thereof having xylanase activity. In another aspect, the polypeptide comprises or consists of the mature polypeptide of SEQ ID NO: 2, SEQ ID NO: 4, or SEQ ID NO: 6. In another aspect, the polypeptide comprises or consists of amino acids 18 to 349 of SEQ ID NO: 2, amino acids 21 to 376 of SEQ ID NO: 4, or amino acids 20 to 396 of SEQ ID NO: 6.

In another embodiment, the present invention relates to an isolated polypeptide having xylanase activity encoded by a polynucleotide that hybridizes under very low stringency conditions, or low stringency conditions, or medium stringency conditions, or medium-high stringency conditions, or high stringency conditions, or very high stringency conditions with (i) the mature polypeptide coding sequence of SEQ ID NO: 1, SEQ ID NO: 3, or SEQ ID NO: 5, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, SEQ ID NO: 3, or SEQ ID NO: 5, or a subsequence thereof, as well as the polypeptide of SEQ ID NO: 2, SEQ ID NO: 4, or SEQ ID NO: 6, or a fragment thereof, may be used to design nucleic acid probes to identify and clone DNA encoding polypeptides having xylanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, or SEQ ID NO: 5 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, or SEQ ID NO: 5; (ii) the mature polypeptide coding sequence of SEQ ID NO: 1, SEQ ID NO: 3, or SEQ ID NO: 5; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, or SEQ ID NO: 6; the mature polypeptide thereof; or a fragment thereof. In another aspect, the nucleic acid probe is SEQ ID NO: 1, SEQ ID NO: 3, or SEQ ID NO: 5; or the cDNA sequence thereof. In another aspect, the nucleic acid probe is the polynucleotide contained in *Lentinus similis* Strain NN048945, wherein the polynucleotide encodes a polypeptide having xylanase activity.

In another embodiment, the present invention relates to an isolated polypeptide having xylanase activity encoded by a polynucleotide having a sequence identity to the mature polypeptide coding sequence of SEQ ID NO: 1, SEQ ID NO: 3, or SEQ ID NO: 5, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, or SEQ ID NO: 6 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, or SEQ ID NO: 6 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having [Enzyme] Activity

A polypeptide having xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Lentinus* polypeptide.

In another aspect, the polypeptide is a *Lentinus similis* polypeptide, e.g., a polypeptide obtained from *Lentinus similis* Strain NN048945.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 18 to 349 of SEQ ID NO: 2), a catalytic domain having at least 60% sequence identity to the catalytic domain of SEQ ID NO: 4 (for example, amino acids 81 to 376 of SEQ ID NO: 4), or a catalytic domain having at least 60% sequence identity to the catalytic domain of SEQ ID NO: 6 (for example, amino acids 82 to 396 of SEQ ID NO: 6);

(b) a catalytic domain encoded by a polynucleotide having at least 60% sequence identity to the catalytic domain coding sequence of SEQ ID NO: 1 (for example, nucleotides 52-246, 300-390, 444-570, 624-625, 685-705, 764-1272, and 1333-1383 of SEQ ID NO: 1), a catalytic domain encoded by a polynucleotide having at least 60% sequence identity to the catalytic domain coding sequence of SEQ ID NO: 35 (for example, nucleotides 353-440, 493-548, 603-609, 667-756, 808-833, 885-980, 1037-1182, 1247-1355, 1408-1480, 1538-1557, 1613-1699, and 1754-1843 of SEQ ID NO: 3), or a catalytic domain encoded by a polynucleotide having at least 60% sequence identity to the catalytic domain coding sequence of SEQ ID NO: 5 (for example, nucleotides 426-569, 635-725, 796-922, 977-978, 1041-1061, 1109-1617, and 1677-1727 of SEQ ID NO: 5);

(c) a variant of a catalytic domain comprising a substitution, deletion, and/or insertion of one or more (several) amino acids of the catalytic domain of SEQ ID NO: 2, SEQ ID NO: 4, or SEQ ID NO: 6; and (d) a fragment of a catalytic domain of (a), (b), or (c), which has xylanase activity.

The catalytic domain preferably has a degree of sequence identity to the catalytic domain of SEQ ID NO: 2, SEQ ID NO: 4, or SEQ ID NO: 6 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, or SEQ ID NO: 6.

The catalytic domain preferably comprises or consists of the catalytic domain of SEQ ID NO: 2 or an allelic variant thereof; or is a fragment thereof having xylanase activity. In another preferred aspect, the catalytic domain comprises or consists of amino acids 18 to 349 of SEQ ID NO: 2.

The catalytic domain preferably comprises or consists of the catalytic domain of SEQ ID NO: 4 or an allelic variant thereof; or is a fragment thereof having xylanase activity. In another preferred aspect, the catalytic domain comprises or consists of amino acids 81 to 376 of SEQ ID NO: 4.

The catalytic domain preferably comprises or consists of the catalytic domain of SEQ ID NO: 6 or an allelic variant thereof; or is a fragment thereof having xylanase activity. In another preferred aspect, the catalytic domain comprises or consists of amino acids 82 to 396 of SEQ ID NO: 6.

In an embodiment, the catalytic domain may be encoded by a polynucleotide that hybridizes under very low stringency conditions, or low stringency conditions, or medium stringency conditions, or medium-high stringency conditions, or high stringency conditions, or very high stringency conditions (as defined above) with (i) the catalytic domain coding sequence of SEQ ID NO: 1, SEQ ID NO: 3, or SEQ ID NO: 5, (ii) the cDNA sequence contained in the catalytic domain coding sequence of SEQ ID NO: 1, SEQ ID NO: 3, or SEQ ID NO: 5, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, or SEQ ID NO: 5 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having xylanase activity.

In one aspect, the polynucleotide encoding the catalytic domain comprises or consists of nucleotides 52 to 1383 of SEQ ID NO: 1 or the cDNA sequence thereof. In particular the polynucleotide encoding the catalytic domain comprises or consists of nucleotides 52-246, 300-390, 444-570, 624-625, 685-705, 764-1272, and 1333-1383 of SEQ ID NO: 1.

In one aspect, the polynucleotide encoding the catalytic domain comprises or consists of nucleotides 353 to 1843 of SEQ ID NO: 3 or the cDNA sequence thereof. In particular the polynucleotide encoding the catalytic domain comprises or consists of nucleotides 353-440, 493-548, 603-609, 667-756, 808-833, 885-980, 1037-1182, 1247-1355, 1408-1480, 1538-1557, 1613-1699, and 1754-1843 of SEQ ID NO: 35.

In one aspect, the polynucleotide encoding the catalytic domain comprises or consists of nucleotides 426 to 1727 of SEQ ID NO: 5 or the cDNA sequence thereof. In particular the polynucleotide encoding the catalytic domain comprises or consists of nucleotides 426-569, 635-725, 796-922, 977-978, 1041-1061, 1109-1617, and 1677-1727 of SEQ ID NO: 5.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Lentinus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, or SEQ ID NO: 5, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus neutral* alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rmB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomy-*

*ces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Lentinus* cell. In a more preferred aspect, the cell is a *Lentinus similis* cell. In a most preferred aspect, the cell is *Lentinus similis* Strain NN048945.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having xylanase activity, or compositions thereof.

The present invention also relates to processes for degrading a cellulosic material or xylan-containing material, comprising: treating the cellulosic material or xylan-containing material with an enzyme composition in the presence of a polypeptide having xylanase activity of the present invention. In one aspect, the processes further comprise recovering the degraded or converted cellulosic material or xylan-containing material. Soluble products of degradation or conversion of the cellulosic material or xylan-containing material can be separated from insoluble cellulosic material or xylan-containing material using a method known in the art such as, for example, centrifugation, filtration, or gravity settling.

The present invention also relates to processes of producing a fermentation product, comprising: (a) saccharifying a cellulosic material or xylan-containing material with an enzyme composition in the presence of a polypeptide having xylanase activity of the present invention; (b) fermenting the saccharified cellulosic material or xylan-containing material with one or more (e.g., several) fermenting microorganisms to produce the fermentation product; and (c) recovering the fermentation product from the fermentation.

The present invention also relates to processes of fermenting a cellulosic material or xylan-containing material, comprising: fermenting the cellulosic material or xylan-containing material with one or more (e.g., several) fermenting microorganisms, wherein the cellulosic material or xylan-containing material is saccharified with an enzyme composition in the presence of a polypeptide having xylanase activity of the present invention. In one aspect, the fermenting of the cellulosic material or xylan-containing material produces a fermentation product. In another aspect, the processes further comprise recovering the fermentation product from the fermentation.

The processes of the present invention can be used to saccharify the cellulosic material or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material or xylan-containing material typically involves pretreatment, enzymatic hydrolysis (saccharification), and fermentation.

The processing of the cellulosic material or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material or xylan-containing material to fermentable sugars, e.g., glucose, cellobiose, and pentose monomers, and then ferment the fermentable sugars to ethanol. In SSF, the enzymatic hydrolysis of the cellulosic material or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-

827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material or xylan-containing material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material or xylan-containing material is heated to disrupt the plant cell wall components, including lignin, hemicellulose, and cellulose to make the cellulose and other fractions, e.g., hemicellulose, accessible to enzymes. The cellulosic material or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material or xylan-containing material is present during pretreatment in amounts preferably between 10-80 wt %, e.g., 20-70 wt % or 30-60 wt %, such as around 40 wt %. The pretreated cellulosic material or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having xylanase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material or xylan-containing material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the cellulase is preferably one or more (e.g., several) enzymes selected from the group consisting of an endoglucanase, a cellobiohydrolase, and a beta-glucosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having xylanase activity depend on several factors including, but not limited to, the mixture of component cellulolytic enzymes, the cellulosic material or xylan-containing material, the concentration of cellulosic material or xylan-containing material, the pretreatment(s) of the cellulosic material or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material or xylan-containing material.

In another aspect, an effective amount of a polypeptide having xylanase activity to the cellulosic material or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material or xylan-containing material.

In another aspect, an effective amount of a polypeptide having xylanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola,*

*Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes A/S), CELLIC™ CTec2 (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus* aculeatus cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/

071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material or xylan-containing material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of thenitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material or xylan-containing material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC™ HTec (Novozymes A/S), CELLIC™ HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8x212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8x211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Preferred xylose fermenting yeast include strains of *Candida,* preferably *C. sheatae* or *C. sonorensis;* and strains of *Pichia,* preferably *P. stipitis,* such as *P. stipitis* CBS 5773. Preferred pentose fermenting yeast include strains of *Pachysolen,* preferably *P. tannophilus.* Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum;* and *Zymomonas,* such as *Zymomonas mobilis.*

In a preferred aspect, the yeast is a *Bretannomyces.* In a more preferred aspect, the yeast is *Bretannomyces clausenii.* In another preferred aspect, the yeast is a *Candida.* In another more preferred aspect, the yeast is *Candida sonorensis.* In another more preferred aspect, the yeast is *Candida boidinii.* In another more preferred aspect, the yeast is *Candida blankii.* In another more preferred aspect, the yeast is *Candida brassicae.* In another more preferred aspect, the yeast is *Candida diddensii.* In another more preferred aspect, the yeast is *Candida entomophiliia.* In another more preferred aspect, the yeast is *Candida pseudotropicalis.* In another more preferred aspect, the yeast is *Candida scehatae.* In another more preferred aspect, the yeast is *Candida utilis.* In another preferred aspect, the yeast is a *Clavispora.* In another more preferred aspect, the yeast is *Clavispora lusitaniae.* In another more preferred aspect, the yeast is *Clavispora opuntiae.* In another preferred aspect, the yeast is a *Kluyveromyces.* In another more preferred aspect, the yeast is *Kluyveromyces fragilis.* In another more preferred aspect, the yeast is *Kluyveromyces marxianus.* In another more preferred aspect, the yeast is *Kluyveromyces thermotolerans.* In another preferred aspect, the yeast is a *Pachysolen.* In another more preferred aspect, the yeast is *Pachysolen tannophilus.* In another preferred aspect, the yeast is a *Pichia.* In another more preferred aspect, the yeast is a *Pichia stipitis.* In another preferred aspect, the yeast is a *Saccharomyces* spp. In a more preferred aspect, the yeast is *Saccharomyces cerevisiae.* In another more preferred aspect, the yeast is *Saccharomyces distaticus.* In another more preferred aspect, the yeast is *Saccharomyces uvarum.*

In a preferred aspect, the bacterium is a *Bacillus.* In a more preferred aspect, the bacterium is *Bacillus coagulans.* In another preferred aspect, the bacterium is a *Clostridium.* In another more preferred aspect, the bacterium is *Clostridium acetobutylicum.* In another more preferred aspect, the bacterium is *Clostridium* phytofermentans. In another more preferred aspect, the bacterium is *Clostridium thermocellum.* In another more preferred aspect, the bacterium is *Geobacilus* sp. In another more preferred aspect, the bacterium is a *Thermoanaerobacter.* In another more preferred aspect, the bacterium is *Thermoanaerobacter saccharolyticum.* In another preferred aspect, the bacterium is a *Zymomonas.* In another more preferred aspect, the bacterium is *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharo-*

*myces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 17 of SEQ ID NO: 2, amino acids 1 to 20 of SEQ ID NO: 4, or amino acids 1 to 19 of SEQ ID NO: 6. The polynucleotide may further comprise a gene encoding a protein, which is operably linked to the signal peptide. The protein is preferably foreign to the signal peptide. In one aspect, the polynucleotide encoding the signal peptide is nucleotides 1 to 51 of SEQ ID NO: 1. In another aspect, the polynucleotide encoding the signal peptide is nucleotides 1 to 60 of SEQ ID NO: 3. In another aspect, the polynucleotide encoding the signal peptide is nucleotides 1 to 57 of SEQ ID NO: 5.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A process for degrading a cellulosic material, comprising treating the cellulosic material with a composition comprising a polypeptide having xylanase activity, a cellobiohydrolase I, a cellobiohydrolase II, an endoglucanase, a beta-qlucosidase, and a GH61 polypeptide, wherein the polypeptide having xylanase activity is selected from the group consisting of:
(a) a polypeptide having at least 95% sequence identity to the sequence of amino acids 18-349 of SEQ ID NO: 2;
(b) a polypeptide encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes in 2×SSC, 0.2% SDS at 65° C.; and
(c) a fragment of the sequence of amino acids 18-349 of SEQ ID NO: 2 that has xylanase activity.

2. A process for producing a fermentation product, comprising:
(a) saccharifying a cellulosic material with a composition comprising a polypeptide having xylanase activity, a cellobiohydrolase I, a cellobiohydrolase II, an endoqlucanase, a beta-qlucosidase, and a GH61 polypeptide, wherein the polypeptide having xylanase activity is selected from the group consisting of:
(1) a polypeptide having at least 95% sequence identity to the sequence of amino acids 18-349 of SEQ ID NO: 2;
(2) a polypeptide encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii), wherein high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes in 2×SSC, 0.2% SDS at 65° C.; and
(3) a fragment of the sequence of amino acids 18-349 of SEQ ID NO: 2 that has xylanase activity; and
(b) fermenting the saccharified cellulosic material with one or more fermenting microorganisms to produce the fermentation product.

3. The process of claim 2, further comprising recovering the fermentation product.

4. A process for degrading a cellulosic material, comprising treating the cellulosic material with a composition comprising a cellobiohydrolase I, a cellobiohydrolase II, an endoglucanase, a beta-glucosidase, a GH61 polypeptide, and a polypeptide comprising a catalytic domain having at least 95% sequence identity to amino acids 18 to 349 of SEQ ID NO: 2, wherein the catalytic domain has xylanase activity.

5. A process for producing a fermentation product, comprising:
(a) saccharifying a cellulosic material with a composition comprising a cellobiohydrolase I, a cellobiohydrolase II, an endoglucanase, a beta-glucosidase, a GH61 polypeptide, and a polypeptide comprising a catalytic domain having at least 95% sequence identity to amino acids 18 to 349 of SEQ ID NO: 2, wherein the catalytic domain has xylanase activity; and
(b) fermenting the saccharified cellulosic material with one or more fermenting microorganisms to produce the fermentation product.

6. The process of claim 5, further comprising recovering the fermentation product.

7. The process of claim 1, wherein the polypeptide having xylanase activity has at least 97% sequence identity to the sequence of amino acids 18-349 of SEQ ID NO: 2.

8. The process of claim 1, wherein the polypeptide having xylanase activity is a variant of the sequence of amino acids 18-349 of SEQ ID NO: 2 comprising a substitution, deletion, and/or insertion at one or more positions and wherein the variant has at least 95% sequence identity to the sequence of amino acids 18-349 of SEQ ID NO: 2.

9. The process of claim 1, wherein the polypeptide having xylanase activity comprises the sequence of amino acids 18-349 of SEQ ID NO: 2.

10. The process of claim 1, further comprising recovering the degraded cellulosic material.

11. The process of claim 2, wherein the polypeptide having xylanase activity has at least 97% sequence identity to the sequence of amino acids 18-349 of SEQ ID NO: 2.

12. The process of claim 2, wherein the polypeptide having xylanase activity is a variant of the sequence of amino acids 18-349 of SEQ ID NO: 2 comprising a substitution, deletion, and/or insertion at one or more positions and wherein the variant has at least 95% sequence identity to the sequence of amino acids 18-349 of SEQ ID NO: 2.

13. The process of claim 2, wherein the polypeptide having xylanase activity comprises the sequence of amino acids 18-349 of SEQ ID NO: 2.

14. The process of claim 2, wherein steps (a) and (b) are performed simultaneously.

15. The process of claim 4, further comprising recovering the degraded cellulosic material.

16. The process of claim 4, wherein the polypeptide comprising a catalytic domain comprises amino acids 18 to 349 of SEQ ID NO: 2, wherein the catalytic domain has xylanase activity.

17. The process of claim 4, wherein the polypeptide comprising a catalytic domain further comprises a cellulose binding domain.

18. The process of claim 5, wherein steps (a) and (b) are performed simultaneously.

19. The process of claim 5, wherein the polypeptide comprising a catalytic domain comprises amino acids 18 to 349 of SEQ ID NO: 2, wherein the catalytic domain has xylanase activity.

20. The process of claim 5, wherein the polypeptide comprising a catalytic domain further comprises a cellulose binding domain.

* * * * *

```
                              SEQUENCE LISTING

<160> NUMBER OF SEQ ID NOS: 6

<210> SEQ ID NO 1
<211> LENGTH: 1386
<212> TYPE: DNA
<213> ORGANISM: Lentinus similis
<220> FEATURE:
<221> NAME/KEY: CDS
<222> LOCATION: (1)..(246)
<220> FEATURE:
<221> NAME/KEY: sig_peptide
<222> LOCATION: (1)..(51)
<220> FEATURE:
<221> NAME/KEY: mat_peptide
<222> LOCATION: (52)..()
<220> FEATURE:
<221> NAME/KEY: Intron
<222> LOCATION: (247)..(299)
<220> FEATURE:
<221> NAME/KEY: CDS
<222> LOCATION: (300)..(390)
<220> FEATURE:
<221> NAME/KEY: Intron
<222> LOCATION: (391)..(443)
<220> FEATURE:
<221> NAME/KEY: CDS
<222> LOCATION: (444)..(570)
<220> FEATURE:
<221> NAME/KEY: Intron
<222> LOCATION: (571)..(623)
<220> FEATURE:
<221> NAME/KEY: CDS
<222> LOCATION: (624)..(625)
<220> FEATURE:
<221> NAME/KEY: Intron
<222> LOCATION: (626)..(684)
<220> FEATURE:
<221> NAME/KEY: CDS
<222> LOCATION: (685)..(705)
<220> FEATURE:
<221> NAME/KEY: Intron
<222> LOCATION: (706)..(763)
<220> FEATURE:
<221> NAME/KEY: CDS
<222> LOCATION: (764)..(1272)
<220> FEATURE:
<221> NAME/KEY: Intron
<222> LOCATION: (1273)..(1332)
<220> FEATURE:
<221> NAME/KEY: CDS
<222> LOCATION: (1333)..(1383)

<400> SEQUENCE: 1 atg aga act aat ctc gtg gcc ctg ctg tcg gcg ata tca ctc gca gca      48
Met Arg Thr Asn Leu Val Ala Leu Leu Ser Ala Ile Ser Leu Ala Ala
        -15                 -10                 -5 tcc gcc cca aca ttc aac ggg acc cta gaa gga cga gcg gca caa gcc      96
Ser Ala Pro Thr Phe Asn Gly Thr Leu Glu Gly Arg Ala Ala Gln Ala
 -1   1               5                  10                  15 aca gag ctt cat gcc ctt gcc aaa caa cat ggc aaa ctg tac ttc ggc     144
Thr Glu Leu His Ala Leu Ala Lys Gln His Gly Lys Leu Tyr Phe Gly
                 20                  25                  30 aca gca acg gac aac cca gag ctc acc gac acg ccg tat gtt gcc atc     192
Thr Ala Thr Asp Asn Pro Glu Leu Thr Asp Thr Pro Tyr Val Ala Ile
             35                  40                  45
```

```
ctc gac gac aac caa atg ttc ggt caa atc aca gct gcc aac agt atg      240
Leu Asp Asp Asn Gln Met Phe Gly Gln Ile Thr Ala Ala Asn Ser Met
             50                  55                  60 aaa tgg gtaagcattt gcctgcgagg agaatggccg ttgctgatgt tctttcatat       296
Lys Trp
 65 tag gac gcg act gaa cct tcc cgt ggc cag ttt acg ttt gcc gca ggc      344
    Asp Ala Thr Glu Pro Ser Arg Gly Gln Phe Thr Phe Ala Ala Gly
                 70                  75                  80 gac gtc att gcg aac ctg gcc aag cag aat ggg caa ttg ctt cga g        390
Asp Val Ile Ala Asn Leu Ala Lys Gln Asn Gly Gln Leu Leu Arg
                 85                  90                  95 gtgtgtcaag cctgtttcta gattttctcg ttcgcctaac aatacatgat tag gg        445
                                                           Gly cat aat tgc gtt tgg cac aac cag ttg cca agc tgg gtg acc gca ggt      493
His Asn Cys Val Trp His Asn Gln Leu Pro Ser Trp Val Thr Ala Gly
                100                 105                 110 cac ttc tcc aag gcg gac ttg cta tcg att gtt cag acc cac tgc agc      541
His Phe Ser Lys Ala Asp Leu Leu Ser Ile Val Gln Thr His Cys Ser
            115                 120                 125 acc ctg gtt gga cat tac aag gga caa gt  gtaagtctgc tactacaccg        590
Thr Leu Val Gly His Tyr Lys Gly Gln Val
            130                 135 atcgaaagct aacggactca cgttctctcc tag c t gtgagtctaa gggcatacta       645
ccttgacaca tactcaagta ctgacgttaa taactgaag ac  gct tgg gat gtc       698
                                              Tyr Ala Trp Asp Val
                                                          140 gtc aat g gtatgttcac agtgcatctc ggtgtggact gcatcccaac cgcattccac     755
Val Asn
145 ataatcag ag  atc atg aat gac aac ggc aca ttt gcg aac gac gtc ttc     804
             Glu Ile Met Asn Asp Asn Gly Thr Phe Ala Asn Asp Val Phe
                         150                 155 ttc agc act aca ggg aca gat tac atc gcc acc gct ttc cgc gct gct      852
Phe Ser Thr Thr Gly Thr Asp Tyr Ile Ala Thr Ala Phe Arg Ala Ala
160                 165                 170                 175 cgc gcc gct gac cct aat gcc aaa cta tat gca aac gac ttc aat atc      900
Arg Ala Ala Asp Pro Asn Ala Lys Leu Tyr Ala Asn Asp Phe Asn Ile
                180                 185                 190 gaa ggc act ggc gca aaa tca acc gcg tac caa aat ctc atc cgt act      948
Glu Gly Thr Gly Ala Lys Ser Thr Ala Tyr Gln Asn Leu Ile Arg Thr
            195                 200                 205 ctc aaa tcc caa ggt gta ccc atc gac ggc atc ggc atg caa tct cac      996
Leu Lys Ser Gln Gly Val Pro Ile Asp Gly Ile Gly Met Gln Ser His
            210                 215                 220 ttc atc gtc ggg gag ctc ccg cca aac atc aaa cag aac ata cag gct     1044
Phe Ile Val Gly Glu Leu Pro Pro Asn Ile Lys Gln Asn Ile Gln Ala
225                 230                 235 ttc acc gcg ctg ggt gtg gaa gtg gcg att aca gag ttg gat gtg agg     1092
Phe Thr Ala Leu Gly Val Glu Val Ala Ile Thr Glu Leu Asp Val Arg
240                 245                 250                 255 atg act ttg cct gct act cag gca ttg ttg caa cag cag cag aag gat     1140
Met Thr Leu Pro Ala Thr Gln Ala Leu Leu Gln Gln Gln Gln Lys Asp
                260                 265                 270 tat cag acg gtg atc cag gct tgc aac gag gtc ccg gga tgc atc ggt     1188
Tyr Gln Thr Val Ile Gln Ala Cys Asn Glu Val Pro Gly Cys Ile Gly
            275                 280                 285
```

```
gtt aca ctt tgg gat ttc acg gat aag ttc tcg tgg gtg cct ggc gcg      1236
Val Thr Leu Trp Asp Phe Thr Asp Lys Phe Ser Trp Val Pro Gly Ala
        290                 295                 300 ttc ccc gga cag ggg gct gca tgc cct tgg gat cag gtacgtaccg            1282
Phe Pro Gly Gln Gly Ala Ala Cys Pro Trp Asp Gln
        305                 310                 315 gaagttctca ctgtgaaatg atctctaacg tgctcacgta ccaatcacag aat ttg        1338
                                                       Asn Leu caa ctc aag cct gcc ttc acc ggt att gtc aat ggc ttc aac tca tga       1386
Gln Leu Lys Pro Ala Phe Thr Gly Ile Val Asn Gly Phe Asn Ser
        320                 325                 330

<210> SEQ ID NO 2
<211> LENGTH: 349
<212> TYPE: PRT
<213> ORGANISM: Lentinus similis

<400> SEQUENCE: 2

Met Arg Thr Asn Leu Val Ala Leu Leu Ser Ala Ile Ser Leu Ala Ala
        -15                 -10                  -5

Ser Ala Pro Thr Phe Asn Gly Thr Leu Glu Gly Arg Ala Ala Gln Ala
 -1   1              5                  10                  15

Thr Glu Leu His Ala Leu Ala Lys Gln His Gly Lys Leu Tyr Phe Gly
                 20                  25                  30

Thr Ala Thr Asp Asn Pro Glu Leu Thr Asp Thr Pro Tyr Val Ala Ile
             35                  40                  45

Leu Asp Asp Asn Gln Met Phe Gly Gln Ile Thr Ala Ala Asn Ser Met
         50                  55                  60

Lys Trp Asp Ala Thr Glu Pro Ser Arg Gly Gln Phe Thr Phe Ala Ala
 65                  70                  75

Gly Asp Val Ile Ala Asn Leu Ala Lys Gln Asn Gly Gln Leu Leu Arg
 80                  85                  90                  95

Gly His Asn Cys Val Trp His Asn Gln Leu Pro Ser Trp Val Thr Ala
                100                 105                 110

Gly His Phe Ser Lys Ala Asp Leu Leu Ser Ile Val Gln Thr His Cys
            115                 120                 125

Ser Thr Leu Val Gly His Tyr Lys Gly Gln Val Tyr Ala Trp Asp Val
        130                 135                 140

Val Asn Glu Ile Met Asn Asp Asn Gly Thr Phe Ala Asn Asp Val Phe
    145                 150                 155

Phe Ser Thr Thr Gly Thr Asp Tyr Ile Ala Thr Ala Phe Arg Ala Ala
160                 165                 170                 175

Arg Ala Ala Asp Pro Asn Ala Lys Leu Tyr Ala Asn Asp Phe Asn Ile
                180                 185                 190

Glu Gly Thr Gly Ala Lys Ser Thr Ala Tyr Gln Asn Leu Ile Arg Thr
            195                 200                 205

Leu Lys Ser Gln Gly Val Pro Ile Asp Gly Ile Gly Met Gln Ser His
        210                 215                 220

Phe Ile Val Gly Glu Leu Pro Pro Asn Ile Lys Gln Asn Ile Gln Ala
    225                 230                 235

Phe Thr Ala Leu Gly Val Glu Val Ala Ile Thr Glu Leu Asp Val Arg
240                 245                 250                 255

Met Thr Leu Pro Ala Thr Gln Ala Leu Leu Gln Gln Gln Lys Asp
                260                 265                 270

Tyr Gln Thr Val Ile Gln Ala Cys Asn Glu Val Pro Gly Cys Ile Gly
            275                 280                 285
```

```
Val Thr Leu Trp Asp Phe Thr Asp Lys Phe Ser Trp Val Pro Gly Ala
            290                 295                 300

Phe Pro Gly Gln Gly Ala Ala Cys Pro Trp Asp Gln Asn Leu Gln Leu
    305                 310                 315

Lys Pro Ala Phe Thr Gly Ile Val Asn Gly Phe Asn Ser
320                 325                 330

<210> SEQ ID NO 3
<211> LENGTH: 1846
<212> TYPE: DNA
<213> ORGANISM: Lentinus similis
<220> FEATURE:
<221> NAME/KEY: CDS
<222> LOCATION: (1)..(79)
<220> FEATURE:
<221> NAME/KEY: sig_peptide
<222> LOCATION: (1)..(60)
<220> FEATURE:
<221> NAME/KEY: mat_peptide
<222> LOCATION: (61)..()
<220> FEATURE:
<221> NAME/KEY: Intron
<222> LOCATION: (80)..(137)
<220> FEATURE:
<221> NAME/KEY: CDS
<222> LOCATION: (138)..(176)
<220> FEATURE:
<221> NAME/KEY: Intron
<222> LOCATION: (177)..(230)
<220> FEATURE:
<221> NAME/KEY: CDS
<222> LOCATION: (231)..(440)
<220> FEATURE:
<221> NAME/KEY: Intron
<222> LOCATION: (441)..(492)
<220> FEATURE:
<221> NAME/KEY: CDS
<222> LOCATION: (493)..(548)
<220> FEATURE:
<221> NAME/KEY: Intron
<222> LOCATION: (549)..(602)
<220> FEATURE:
<221> NAME/KEY: CDS
<222> LOCATION: (603)..(609)
<220> FEATURE:
<221> NAME/KEY: Intron
<222> LOCATION: (610)..(666)
<220> FEATURE:
<221> NAME/KEY: CDS
<222> LOCATION: (667)..(756)
<220> FEATURE:
<221> NAME/KEY: Intron
<222> LOCATION: (757)..(807)
<220> FEATURE:
<221> NAME/KEY: CDS
<222> LOCATION: (808)..(833)
<220> FEATURE:
<221> NAME/KEY: Intron
<222> LOCATION: (834)..(884)
<220> FEATURE:
<221> NAME/KEY: CDS
<222> LOCATION: (885)..(980)
<220> FEATURE:
<221> NAME/KEY: Intron
<222> LOCATION: (981)..(1036)
<220> FEATURE:
<221> NAME/KEY: CDS
<222> LOCATION: (1037)..(1182)
<220> FEATURE:
<221> NAME/KEY: Intron
<222> LOCATION: (1183)..(1246)
<220> FEATURE:
<221> NAME/KEY: CDS
<222> LOCATION: (1247)..(1355)
```

```
<220> FEATURE:
<221> NAME/KEY: Intron
<222> LOCATION: (1356)..(1407)
<220> FEATURE:
<221> NAME/KEY: CDS
<222> LOCATION: (1408)..(1480)
<220> FEATURE:
<221> NAME/KEY: Intron
<222> LOCATION: (1481)..(1537)
<220> FEATURE:
<221> NAME/KEY: CDS
<222> LOCATION: (1538)..(1557)
<220> FEATURE:
<221> NAME/KEY: Intron
<222> LOCATION: (1558)..(1612)
<220> FEATURE:
<221> NAME/KEY: CDS
<222> LOCATION: (1613)..(1699)
<220> FEATURE:
<221> NAME/KEY: Intron
<222> LOCATION: (1700)..(1753)
<220> FEATURE:
<221> NAME/KEY: CDS
<222> LOCATION: (1754)..(1843)

<400> SEQUENCE: 3 atg aag tcc ctc gct gcc ttc gtc gct tta gcc gct gct ttg tct ggc         48
Met Lys Ser Leu Ala Ala Phe Val Ala Leu Ala Ala Ala Leu Ser Gly
-20             -15                 -10                 -5 tct gcc aac gca gta gca gtt tgg ggc caa t gtatgtcgcg tcctatcatc         99
Ser Ala Asn Ala Val Ala Val Trp Gly Gln
        -1  1                 5 ctgttcctca cttttcgcta actacattat tgtctcag gc  ggg gta tgt caa att       154
                                            Cys Gly Val Cys Gln Ile
                                                                10 cct gct atg tta acg aat ggc g gtattgagag agattagggc attggttatt          206
Pro Ala Met Leu Thr Asn Gly
            15 ccgggtcgac tgtctgcgac gcag gc  act aca tgt gtc aag ttg aat gac          256
                            Gly Thr Thr Cys Val Lys Leu Asn Asp
                                 20                  25 tac tac tcc caa tgc cag cct ggg gct gcc aca tcg cca ccc gcg acg         304
Tyr Tyr Ser Gln Cys Gln Pro Gly Ala Ala Thr Ser Pro Pro Ala Thr
 30                  35                  40 aca tca caa ccg gcc ccc aca ggt tcg ccc gct ccc gcc gcg agt gga         352
Thr Ser Gln Pro Ala Pro Thr Gly Ser Pro Ala Pro Ala Ala Ser Gly
45                  50                  55                  60 ctg gcc gcc gct ttt gct aaa aag ggc aag ttg ttc tgg gga act gca         400
Leu Ala Ala Ala Phe Ala Lys Lys Gly Lys Leu Phe Trp Gly Thr Ala
                65                  70                  75 tcg gac tcc aac aga ttc aac gac gca aag gat tcc caa g gtaaacacgc        450
Ser Asp Ser Asn Arg Phe Asn Asp Ala Lys Asp Ser Gln
        80                  85 acttcacaac ggataatgcc cttactcagg acgcccattc ag tg  aca atc gcc         503
                                                 Val Thr Ile Ala
                                                              90 aac ttc aac agt ctt acc ccc gaa aac tcc atg aag tgg gat gca            548
Asn Phe Asn Ser Leu Thr Pro Glu Asn Ser Met Lys Trp Asp Ala
 95                  100                 105 gtaagcgttg ttcttctcat catcggacgt gatccatatt gattgtatat gcag act        605
                                                              Thr gag c gtaagtttgc ggtttgtact gttccctatt ggttgtaaat gccactattc          659
Glu
110
```

```
tccatag cc agc cgt ggt cag ttc tcc ttc tct ggt gcg gac gca cta         707
        Pro Ser Arg Gly Gln Phe Ser Phe Ser Gly Ala Asp Ala Leu
                115                 120 gtc aac tac gcc agc cag cac gga atg tta gtt cgt gct cac acg ttg g      756
Val Asn Tyr Ala Ser Gln His Gly Met Leu Val Arg Ala His Thr Leu
125                 130                 135                 140 gtttgtcgtt catacctcag gtcgaatgtg cgtagactga catatctcca g tt  tgg       812
                                                        Val Trp cat tct cag ctc cca tca tgg gtatgatcat ggacatgtc gtcctttatc            863
His Ser Gln Leu Pro Ser Trp
        145 agctactcat tcggagtcta g gtc tct tcc att tcg gac aaa aca acg ctg        914
                        Val Ser Ser Ile Ser Asp Lys Thr Thr Leu
                            150                 155 acc tca gtc att caa aac cac att tcc act gtc gcc gga aga tat aaa        962
Thr Ser Val Ile Gln Asn His Ile Ser Thr Val Ala Gly Arg Tyr Lys
160                 165                 170                 175 gga aag gtt agg tct tgg gtatgtacta cctctttcac ctcgaagcgt               1010
Gly Lys Val Arg Ser Trp
            180 gtcatatatc tgattattcc tgacag gat gtt gtc aac gag atc ttc aac gag       1063
                        Asp Val Val Asn Glu Ile Phe Asn Glu
                                185                 190 gat gga acg ttc cgc tca tcc gtc ttc tac aat gtg ctc ggc caa agc        1111
Asp Gly Thr Phe Arg Ser Ser Val Phe Tyr Asn Val Leu Gly Gln Ser
                195                 200                 205 ttc gtt act ctc gcg ttc caa gct gcc agg caa gca gat cct aac gcc        1159
Phe Val Thr Leu Ala Phe Gln Ala Ala Arg Gln Ala Asp Pro Asn Ala
            210                 215                 220 aag ctg tac atc aac gac tac aa  gtaggtcact acgcggccta ttgttgaacg       1212
Lys Leu Tyr Ile Asn Asp Tyr Asn
                225                 230 gttcatgcaa ttaattgaca acaatcgtgt acag c ttg gat agc gcc aat gcc        1265
                                      Leu Asp Ser Ala Asn Ala
                                                        235 aag ttg acg gcc gtt gtc aac ctt gtg aag cag att aac aat agc ggt        1313
Lys Leu Thr Ala Val Val Asn Leu Val Lys Gln Ile Asn Asn Ser Gly
            240                 245                 250 acg aag ctc atc gac ggt atc ggt act cag atg cac ctc tcg                1355
Thr Lys Leu Ile Asp Gly Ile Gly Thr Gln Met His Leu Ser
255                 260                 265 gttcgttacc aaaccaattg tttgttacga tagttgtgct tatttcatcc ag gct gga      1413
                                                        Ala Gly ggc gcg gga ggt gcc cag gcg gct ctc cag ctt gct gcg act gct ggt        1461
Gly Ala Gly Gly Ala Gln Ala Ala Leu Gln Leu Ala Ala Thr Ala Gly
                270                 275                 280 gtc gag gtt gct atc acc g gtgagttatt gcagggcatg aacgtgatcg             1510
Val Glu Val Ala Ile Thr
285                 290 caggatactg atatcacttc gatccag aa  ttg gat att gcg aat gct              1557
                                  Glu Leu Asp Ile Ala Asn Ala
                                                        295 gtacgtcttt tcacgctact tgaggcataa cttttttgac gtggcctttc ctcag gcc       1615
                                                                Ala ccc aac gac tat gtt acc gtc gtg aaa gct tgc ttg gct gtc tct aac        1663
Pro Asn Asp Tyr Val Thr Val Val Lys Ala Cys Leu Ala Val Ser Asn
300                 305                 310
```

-continued

```
tgc gta tct atc acg agc tgg ggt gtc agt gac aag gtcaggcatc      1709
Cys Val Ser Ile Thr Ser Trp Gly Val Ser Asp Lys
315                 320                 325 ctttgctcac ctttgctacc tatacagctg aactttcctc gcag gac tct tgg cgt   1765
                                                 Asp Ser Trp Arg
                                                             330 gca tcc acg aac cct ctg ctc ttc gat gct aac ttt aac cct aag cct   1813
Ala Ser Thr Asn Pro Leu Leu Phe Asp Ala Asn Phe Asn Pro Lys Pro
                335                 340                 345 gca tac act gcc atc ttg cag gca ctt gcc taa                       1846
Ala Tyr Thr Ala Ile Leu Gln Ala Leu Ala
            350                 355
```

<210> SEQ ID NO 4
<211> LENGTH: 376
<212> TYPE: PRT
<213> ORGANISM: Lentinus similis

<400> SEQUENCE: 4

```
Met Lys Ser Leu Ala Ala Phe Val Ala Leu Ala Ala Leu Ser Gly
-20             -15                 -10                 -5

Ser Ala Asn Ala Val Ala Val Trp Gly Gln Cys Gly Val Cys Gln Ile
        -1  1               5                   10

Pro Ala Met Leu Thr Asn Gly Gly Thr Thr Cys Val Lys Leu Asn Asp
            15                  20                  25

Tyr Tyr Ser Gln Cys Gln Pro Gly Ala Ala Thr Ser Pro Pro Ala Thr
        30                  35                  40

Thr Ser Gln Pro Ala Pro Thr Gly Ser Pro Ala Pro Ala Ala Ser Gly
45                  50                  55                  60

Leu Ala Ala Ala Phe Ala Lys Lys Gly Lys Leu Phe Trp Gly Thr Ala
                65                  70                  75

Ser Asp Ser Asn Arg Phe Asn Asp Ala Lys Asp Ser Gln Val Thr Ile
                80                  85                  90

Ala Asn Phe Asn Ser Leu Thr Pro Glu Asn Ser Met Lys Trp Asp Ala
            95                  100                 105

Thr Glu Pro Ser Arg Gly Gln Phe Ser Phe Ser Gly Ala Asp Ala Leu
        110                 115                 120

Val Asn Tyr Ala Ser Gln His Gly Met Leu Val Arg Ala His Thr Leu
125                 130                 135                 140

Val Trp His Ser Gln Leu Pro Ser Trp Val Ser Ile Ser Asp Lys
                145                 150                 155

Thr Thr Leu Thr Ser Val Ile Gln Asn His Ile Ser Thr Val Ala Gly
            160                 165                 170

Arg Tyr Lys Gly Lys Val Arg Ser Trp Asp Val Val Asn Glu Ile Phe
        175                 180                 185

Asn Glu Asp Gly Thr Phe Arg Ser Ser Val Phe Tyr Asn Val Leu Gly
190                 195                 200

Gln Ser Phe Val Thr Leu Ala Phe Gln Ala Ala Arg Gln Ala Asp Pro
205                 210                 215                 220

Asn Ala Lys Leu Tyr Ile Asn Asp Tyr Asn Leu Asp Ser Ala Asn Ala
                225                 230                 235

Lys Leu Thr Ala Val Val Asn Leu Val Lys Gln Ile Asn Asn Ser Gly
            240                 245                 250

Thr Lys Leu Ile Asp Gly Ile Gly Thr Gln Met His Leu Ser Ala Gly
        255                 260                 265
```

```
Gly Ala Gly Gly Ala Gln Ala Ala Leu Gln Leu Ala Ala Thr Ala Gly
            270                 275                 280

Val Glu Val Ala Ile Thr Glu Leu Asp Ile Ala Asn Ala Ala Pro Asn
285                 290                 295                 300

Asp Tyr Val Thr Val Val Lys Ala Cys Leu Ala Val Ser Asn Cys Val
                305                 310                 315

Ser Ile Thr Ser Trp Gly Val Ser Asp Lys Asp Ser Trp Arg Ala Ser
                320                 325                 330

Thr Asn Pro Leu Leu Phe Asp Ala Asn Phe Asn Pro Lys Pro Ala Tyr
            335                 340                 345

Thr Ala Ile Leu Gln Ala Leu Ala
            350                 355

<210> SEQ ID NO 5
<211> LENGTH: 1730
<212> TYPE: DNA
<213> ORGANISM: Lentinus similis
<220> FEATURE:
<221> NAME/KEY: CDS
<222> LOCATION: (1)..(79)
<220> FEATURE:
<221> NAME/KEY: sig_peptide
<222> LOCATION: (1)..(57)
<220> FEATURE:
<221> NAME/KEY: mat_peptide
<222> LOCATION: (58)..()
<220> FEATURE:
<221> NAME/KEY: Intron
<222> LOCATION: (80)..(141)
<220> FEATURE:
<221> NAME/KEY: CDS
<222> LOCATION: (142)..(152)
<220> FEATURE:
<221> NAME/KEY: Intron
<222> LOCATION: (153)..(210)
<220> FEATURE:
<221> NAME/KEY: CDS
<222> LOCATION: (211)..(291)
<220> FEATURE:
<221> NAME/KEY: Intron
<222> LOCATION: (292)..(353)
<220> FEATURE:
<221> NAME/KEY: CDS
<222> LOCATION: (354)..(569)
<220> FEATURE:
<221> NAME/KEY: Intron
<222> LOCATION: (570)..(634)
<220> FEATURE:
<221> NAME/KEY: CDS
<222> LOCATION: (635)..(725)
<220> FEATURE:
<221> NAME/KEY: Intron
<222> LOCATION: (726)..(795)
<220> FEATURE:
<221> NAME/KEY: CDS
<222> LOCATION: (796)..(922)
<220> FEATURE:
<221> NAME/KEY: Intron
<222> LOCATION: (923)..(976)
<220> FEATURE:
<221> NAME/KEY: CDS
<222> LOCATION: (977)..(978)
<220> FEATURE:
<221> NAME/KEY: Intron
<222> LOCATION: (979)..(1040)
<220> FEATURE:
<221> NAME/KEY: CDS
<222> LOCATION: (1041)..(1061)
<220> FEATURE:
<221> NAME/KEY: Intron
<222> LOCATION: (1062)..(1108)
```

```
<220> FEATURE:
<221> NAME/KEY: CDS
<222> LOCATION: (1109)..(1617)
<220> FEATURE:
<221> NAME/KEY: Intron
<222> LOCATION: (1618)..(1676)
<220> FEATURE:
<221> NAME/KEY: CDS
<222> LOCATION: (1677)..(1727)

<400> SEQUENCE: 5 atg aag ctt tct ggt acg ctt gcc gct ctt atc gcc att ctc ccc ttt       48
Met Lys Leu Ser Gly Thr Leu Ala Ala Leu Ile Ala Ile Leu Pro Phe
            -15                 -10                 -5 gca gct gca caa tct caa gag tgg ggt caa t gtaagcctte catacgacte        99
Ala Ala Ala Gln Ser Gln Glu Trp Gly Gln
 -1   1               5 atcgttagtg aaactgtgga ttgctgactc ttatttcaat ag gt  ggc ggg att        152
                                                  Cys Gly Gly Ile
                                                           10 gtgagtatat ataggtcttt tcaggcaact ttgcaatatg aagctcagaa tcctgtag       210 ggc tgg act ggt ccg aca aca tgc gtt gcc gga acc atc tgt gtc aag      258
Gly Trp Thr Gly Pro Thr Thr Cys Val Ala Gly Thr Ile Cys Val Lys
         15                  20                  25 cag aac gat tac tac tct cag tgc ctt cca tct gtcagtctgc catcatgcgt    311
Gln Asn Asp Tyr Tyr Ser Gln Cys Leu Pro Ser
         30                  35 cctcatgaag acgtctttga ctcagttaca tgttttattt ag acc tcg gtt ccc      365
                                                Thr Ser Val Pro
                                                         40 act tcc gtt ccc ccg cct acc agc acc gtg tct tca cct gga tcg acg    413
Thr Ser Val Pro Pro Pro Thr Ser Thr Val Ser Ser Pro Gly Ser Thr
         45                  50                  55 cca acg gca ggt ctc aat agt atc gcc cag gcc cat ggc ctg acc tac    461
Pro Thr Ala Gly Leu Asn Ser Ile Ala Gln Ala His Gly Leu Thr Tyr
         60                  65                  70 ttc ggc tct gcc acg gac aac cca gag ctt tct gac cag gcc tat gtc    509
Phe Gly Ser Ala Thr Asp Asn Pro Glu Leu Ser Asp Gln Ala Tyr Val
75                   80                  85                  90 gcc atc ctc agc gac aac act atg ttc ggt cag atc aca cct gga aac    557
Ala Ile Leu Ser Asp Asn Thr Met Phe Gly Gln Ile Thr Pro Gly Asn
             95                 100                 105 agt atg aaa tgg gtacgttcgt ggctcaagca tgcagggagt acgcgactga        609
Ser Met Lys Trp
            110 ccagcaacat tatttggaat cgtag gat gct act gag cct tct cga ggt act    661
                            Asp Ala Thr Glu Pro Ser Arg Gly Thr
                                             115 ttc act ttc tcc gga ggt gat gtg atc gca aac ctc gcc aag acg aat    709
Phe Thr Phe Ser Gly Gly Asp Val Ile Ala Asn Leu Ala Lys Thr Asn
120                 125                 130                 135 ggg caa ttg ctc cga g gtatgcacgc tttcattcat tctctacatg ggatggaaaa  765
Gly Gln Leu Leu Arg
             140 gatacggtac ttatgacggt tctctcgtag gg  cat aac tgt gtt tgg tac aat   818
                                    Gly His Asn Cys Val Trp Tyr Asn
                                                         145 cag ctt cct tcc tgg gta tcc tct gga aac ttc gat gct ccc acc ttg    866
Gln Leu Pro Ser Trp Val Ser Ser Gly Asn Phe Asp Ala Pro Thr Leu
         150                 155                 160
```

```
acg tcc atc gtg cag act cat tgc agc act ctt gtt ggt cat tac aag      914
Thr Ser Ile Val Gln Thr His Cys Ser Thr Leu Val Gly His Tyr Lys
165                 170                 175                 180 ggt caa at  gtgagtaatt ctatttctat gatctccgaa acagactgaa              962
Gly Gln Ile tgatgctctt tcag t t gtgtgtggaa ttcaatgtcg cgatcataac gttgactgat     1018
gttttgcttt gacattcgaa ag at  tct tgg gat gtt atc aac g gtgagttatt   1071
                            Tyr Ser Trp Asp Val Ile Asn
                                185                 190 ctctcgccgt ccctgagctt gtatctaact cgaacag aa  ccc ttc aac gat gac    1125
                                            Glu Pro Phe Asn Asp Asp
                                                            195 ggt act tgg cgc cag gac gtc ttc tac aac gta ttg ggc aca agc tac     1173
Gly Thr Trp Arg Gln Asp Val Phe Tyr Asn Val Leu Gly Thr Ser Tyr
        200                 205                 210 gtt cag att gcc tta gag gct gcc cgt gct gcc gac cct gcg gcc aag     1221
Val Gln Ile Ala Leu Glu Ala Ala Arg Ala Ala Asp Pro Ala Ala Lys
            215                 220                 225 ctg tac att aac gac tac aac atc gaa ggt cct gga gcc aag gcc acc     1269
Leu Tyr Ile Asn Asp Tyr Asn Ile Glu Gly Pro Gly Ala Lys Ala Thr
230                 235                 240 gcc atg cag aac ctc atc aag acc ctc aag acc aac aac gta ccc atc     1317
Ala Met Gln Asn Leu Ile Lys Thr Leu Lys Thr Asn Asn Val Pro Ile
245                 250                 255                 260 gat ggt gtc ggt ctt caa ggt cac ttc atc gtc ggc gct ctc ccc tct     1365
Asp Gly Val Gly Leu Gln Gly His Phe Ile Val Gly Ala Leu Pro Ser
                265                 270                 275 ggc att cag cag aac atc cag gct ttc gtg aac ctc ggc gtt gag gtc     1413
Gly Ile Gln Gln Asn Ile Gln Ala Phe Val Asn Leu Gly Val Glu Val
        280                 285                 290 gcc atc acc gag cta gat att agg acg acc act ccc gcg tcg tct tct     1461
Ala Ile Thr Glu Leu Asp Ile Arg Thr Thr Thr Pro Ala Ser Ser Ser
            295                 300                 305 gct ctt cag cag cag gcg aag gat tat gcg act gtg gtc acg gca tgt     1509
Ala Leu Gln Gln Gln Ala Lys Asp Tyr Ala Thr Val Val Thr Ala Cys
310                 315                 320 cgt gct gtg aag ggt tgt att ggt atc acc gtc tgg gac tac aca gac     1557
Arg Ala Val Lys Gly Cys Ile Gly Ile Thr Val Trp Asp Tyr Thr Asp
325                 330                 335                 340 aag tac tct tgg gtt ccg tcg acc ttc tct ggt cag ggt gct gct tgc     1605
Lys Tyr Ser Trp Val Pro Ser Thr Phe Ser Gly Gln Gly Ala Ala Cys
                345                 350                 355 ccg tgg gac cag gtgagttatc tataggcttc tctgctgtgt actgcggtct         1657
Pro Trp Asp Gln
            360 gagacgcgcc gacccgcag aac ctc caa cca aag cca gcg tac acc agt att    1709
                    Asn Leu Gln Pro Lys Pro Ala Tyr Thr Ser Ile
                                    365                 370 gca caa tcg ttg gct gcc taa                                         1730
Ala Gln Ser Leu Ala Ala
            375

<210> SEQ ID NO 6
<211> LENGTH: 396
<212> TYPE: PRT
<213> ORGANISM: Lentinus similis
```

```
<400> SEQUENCE: 6

Met Lys Leu Ser Gly Thr Leu Ala Ala Leu Ile Ala Ile Leu Pro Phe
            -15                 -10                 -5
Ala Ala Ala Gln Ser Gln Glu Trp Gly Gln Cys Gly Gly Ile Gly Trp
        -1   1               5                  10
Thr Gly Pro Thr Thr Cys Val Ala Gly Thr Ile Cys Val Lys Gln Asn
         15              20              25
Asp Tyr Tyr Ser Gln Cys Leu Pro Ser Thr Ser Val Pro Thr Ser Val
 30              35              40              45
Pro Pro Pro Thr Ser Thr Val Ser Ser Pro Gly Ser Thr Pro Thr Ala
             50              55              60
Gly Leu Asn Ser Ile Ala Gln Ala His Gly Leu Thr Tyr Phe Gly Ser
             65              70              75
Ala Thr Asp Asn Pro Glu Leu Ser Asp Gln Ala Tyr Val Ala Ile Leu
             80              85              90
Ser Asp Asn Thr Met Phe Gly Gln Ile Thr Pro Gly Asn Ser Met Lys
         95             100             105
Trp Asp Ala Thr Glu Pro Ser Arg Gly Thr Phe Thr Phe Ser Gly Gly
110             115             120             125
Asp Val Ile Ala Asn Leu Ala Lys Thr Asn Gly Gln Leu Leu Arg Gly
             130             135             140
His Asn Cys Val Trp Tyr Asn Gln Leu Pro Ser Trp Val Ser Ser Gly
         145             150             155
Asn Phe Asp Ala Pro Thr Leu Thr Ser Ile Val Gln Thr His Cys Ser
         160             165             170
Thr Leu Val Gly His Tyr Lys Gly Gln Ile Tyr Ser Trp Asp Val Ile
         175             180             185
Asn Glu Pro Phe Asn Asp Asp Gly Thr Trp Arg Gln Asp Val Phe Tyr
190             195             200             205
Asn Val Leu Gly Thr Ser Tyr Val Gln Ile Ala Leu Glu Ala Ala Arg
             210             215             220
Ala Ala Asp Pro Ala Ala Lys Leu Tyr Ile Asn Asp Tyr Asn Ile Glu
             225             230             235
Gly Pro Gly Ala Lys Ala Thr Ala Met Gln Asn Leu Ile Lys Thr Leu
             240             245             250
Lys Thr Asn Asn Val Pro Ile Asp Gly Val Gly Leu Gln Gly His Phe
         255             260             265
Ile Val Gly Ala Leu Pro Ser Gly Ile Gln Gln Asn Ile Gln Ala Phe
270             275             280             285
Val Asn Leu Gly Val Glu Val Ala Ile Thr Glu Leu Asp Ile Arg Thr
             290             295             300
Thr Thr Pro Ala Ser Ser Ala Leu Gln Gln Ala Lys Asp Tyr
             305             310             315
Ala Thr Val Val Thr Ala Cys Arg Ala Val Lys Gly Cys Ile Gly Ile
             320             325             330
Thr Val Trp Asp Tyr Thr Asp Lys Tyr Ser Trp Val Pro Ser Thr Phe
         335             340             345
Ser Gly Gln Gly Ala Ala Cys Pro Trp Asp Gln Asn Leu Gln Pro Lys
350             355             360             365
Pro Ala Tyr Thr Ser Ile Ala Gln Ser Leu Ala Ala
             370             375
```